US008377475B2

(12) United States Patent
Kamath et al.

(10) Patent No.: US 8,377,475 B2
(45) Date of Patent: *Feb. 19, 2013

(54) TABLET CONTAINING CETIRIZINE, PSEUDOEPHEDRINE, AND NAPROXEN CONTAINING A BARRIER LAYER

(75) Inventors: Satish Kamath, Mason, OH (US); Indukumar G. Shah, North Wales, PA (US); Michael Nichols, Somerset, NJ (US); Dinesh Patel, Kendall Park, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 44 days.

This patent is subject to a terminal disclaimer.

(21) Appl. No.: 12/651,497

(22) Filed: Jan. 4, 2010

(65) Prior Publication Data
US 2010/0172985 A1  Jul. 8, 2010

Related U.S. Application Data

(60) Provisional application No. 61/142,431, filed on Jan. 5, 2009.

(51) Int. Cl.
*A61K 9/24* (2006.01)

(52) U.S. Cl. ............ 424/472; 514/255.04; 514/569; 514/646; 514/724; 514/730; 514/740; 514/741

(58) Field of Classification Search .......... 424/472; 514/255.04, 569, 646, 724, 730, 740, 741
See application file for complete search history.

(56) References Cited

U.S. PATENT DOCUMENTS

| | | | |
|---|---|---|---|
| 5,215,755 A | 6/1993 | Roche et al. | |
| 5,817,340 A | 10/1998 | Roche et al. | |
| 6,051,585 A | 4/2000 | Weinstein et al. | |
| 6,171,618 B1 | 1/2001 | Johnson et al. | |
| 6,469,009 B1 | 10/2002 | Van De Venne et al. | |
| 6,489,329 B2 | 12/2002 | Van de Venne et al. | |
| 6,537,573 B2 | 3/2003 | Johnson et al. | |
| 6,613,357 B2 | 9/2003 | Faour et al. | |
| 6,767,200 B2 | 7/2004 | Sowden et al. | |
| 6,780,435 B2 | 8/2004 | Chen et al. | |
| 6,814,979 B2 | 11/2004 | Rudnic et al. | |
| 7,014,867 B2 * | 3/2006 | Fanara et al. | 424/472 |
| 7,217,429 B2 | 5/2007 | Garcia et al. | |
| 7,226,614 B2 | 6/2007 | Fanara et al. | |
| 7,332,183 B2 | 2/2008 | Plachetka et al. | |
| 7,488,497 B2 | 2/2009 | Depui et al. | |
| 2002/0119196 A1 | 8/2002 | Parikh et al. | |
| 2003/0069255 A1 | 4/2003 | Plachetka | |
| 2003/0109453 A1 | 6/2003 | Catania et al. | |
| 2004/0156902 A1 | 8/2004 | Lee et al. | |
| 2004/0253311 A1 | 12/2004 | Berlin et al. | |
| 2005/0249799 A1 | 11/2005 | Jacob et al. | |
| 2006/0057205 A1 | 3/2006 | Srinivasan | |
| 2006/0240105 A1 | 10/2006 | Devane et al. | |
| 2010/0172980 A1 | 7/2010 | Kamath et al. | |
| 2010/0172987 A1 * | 7/2010 | Kamath et al. | 424/475 |

FOREIGN PATENT DOCUMENTS

| | | |
|---|---|---|
| EP | 0348683 A1 | 1/1990 |
| EP | 1392241 B1 | 7/2009 |
| WO | WO 99/15173 A1 | 4/1999 |
| WO | WO 2004/056320 A2 | 7/2004 |
| WO | WO-2005/120465 A2 * | 12/2005 |
| WO | WO 2005/120465 A2 | 12/2005 |
| WO | WO 2007/021968 A2 | 2/2007 |

OTHER PUBLICATIONS

Dinç et al., "Chemometric determination of naproxen sodium and pseudoephedrine hydrochloride in tablets by HPLC," Chem Pharm Bull (Tokyo) Apr. 2006; 54(4):415-21.

Ekpe et al., "High-Performance Liquid Chromatographic Method Development and Validation for the Simultaneous Quantitation of Naproxen Sodium and Pseudoephedrine Hydrochloride Impurities," J Chromatogr Sci. Mar. 2001;39(3):81-6 Abstract.

Fiesco et al., "Bioequivalence study of a new combination of naproxen sodium plus pseudoephedrine capsules in a Mexican sample population," Proc West Pharmacol Soc. 1994;37:161-2.

Gallardo et al., "Symptomatic treatment of common cold in children with a new combination of naproxen sodium plus pseudoephedrine hydrochloride: a comparative trial against pseudoephedrine syrup", Proc West Pharmacol Soc. 1994; 37:161-2.

Leiberman et al., "Pharmaceutical Dosage Forms—Tablets," vol. 3, Chapter 3: "Particle Coating Methods," 1990.

Gupta,P.K., Remington: The Science and Practice of Pharmacy, "Solutions and Phase Equilibria," Chapter 16, pp. 208-226, 2000.

International Search Report dated Mar. 3, 2010 for PCT/US2010/020023.

* cited by examiner

*Primary Examiner* — Ali Soroush
(74) *Attorney, Agent, or Firm* — William E. McGowan

(57) ABSTRACT

In one aspect, the present invention features a tablet including: (i) a first drug layer including naproxen; (ii) a second drug layer including a decongestant (e.g., pseudoephedrine) wherein said second drug layer is a sustained release layer adapted to deliver a therapeutically effective amount of pseudoephedrine for a period of at least twelve hours; and (iii) a barrier layer that does not include naproxen, wherein the barrier layer is in contact with the first drug layer; and (iv) a third drug layer including cetirizine, wherein the third drug layer is in contact with the barrier layer and is not in contact with the first drug layer.

20 Claims, No Drawings

TABLET CONTAINING CETIRIZINE, PSEUDOEPHEDRINE, AND NAPROXEN CONTAINING A BARRIER LAYER

CROSS REFERENCE TO RELATED APPLICATIONS

This application claims benefit of U.S. Provisional Application No. 61/142,431 filed Jan. 5, 2009. The complete disclosure of the aforementioned related U.S. patent application is hereby incorporated herein by reference for all purposes.

BACKGROUND OF THE INVENTION

Many upper respiratory allergy sufferers also suffer nasal congestion and headaches or other associated pains. Thus, there is a need for a product that can treat all three of these symptoms, preferably a single tablet that can treat such symptoms for over a period of eight hours. However, combining pharmaceutically active agents into a single tablet often creates difficulties. First, the duration of action for pharmaceutically active agents are often different, and thus, extended release of one or more of the pharmaceutically active agents may be required. Also, pharmaceutically active agents may be incompatible in that they react and degrade when combined with each other.

Both of these issues exist with the combination of the antihistamine cetirizine, the nasal decongestant pseudoephedrine, and the analgesic naproxen. While naproxen is approved for use up to twelve hours and cetirizine is approved for up to twenty-four hours (both without extended release modifications), pseudoephedrine is not. Also, applicants have discovered that cetirizine degrades in the physical presence of both pseudoephedrine and naproxen when combined in a tablet.

Thus, the present invention relates to a novel tablet that contains these three pharmaceutically active agents.

SUMMARY OF THE INVENTION

In one aspect, the present invention features a tablet including: (i) a first drug layer including naproxen; (ii) a second drug layer including a decongestant (e.g., pseudoephedrine) wherein said second drug layer is a sustained release layer adapted to deliver a therapeutically effective amount of the decongestant for a period of at least four hours (e.g., at least twelve hours); and (iii) a barrier layer that does not include naproxen, wherein the barrier layer is in contact with the first drug layer; and (iv) a third drug layer including cetirizine, wherein the third drug layer is in contact with the barrier layer and is not in contact with the first drug layer.

In another aspect, the present invention features a method of manufacturing a tablet wherein the method includes: (i) preparing a first powder mixture including naproxen utilizing a granulation process; (ii) preparing a second powder mixture including a decongestant (e.g., pseudoephedrine) utilizing a granulation or a dry blending process; (iii) compressing the first powder mixture together with the second powder mixture to form a tablet core such that the first powder mixture forms the first drug layer and the second powder mixture forms the second drug layer; (iv) applying a barrier layer to the tablet core; and (v) applying a third drug layer including cetirizine to the barrier layer.

In another aspect, the present invention features a method of treating symptoms of upper respiratory allergies, nasal congestion, and headache (e.g., for at least for at least twelve hours) by administering a tablet including naproxen, cetirizine, and a decongestant to a person in need to such treatment.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

"Water soluble," as used herein in connection with non-polymeric materials, shall mean from sparingly soluble to very soluble, i.e., not more than 100 parts water required to dissolve 1 part of the non-polymeric, water soluble solute. See Remington, The Science and Practice of Pharmacy, pp 208-209 (2000). "Water soluble," as used herein in connection with polymeric materials, shall mean that the polymer swells in water and can be dispersed at the molecular level or dissolved in water. "Water swellable," as used herein in connection with polymeric materials, shall mean that the polymer swells in water but is not dispersed at the molecular level or dissolved in water.

"Modified release" as used herein refers to the release rate for the pharmaceutically active agent from the tablet or drug layer other than immediate release, including but not limited to sustained, pulsatile, and enteric release.

As used herein, the term "substantially covers" means covering at least 50%, such as at least 75%, such as at least 90%, such as at least 95%, such as at least 99% of a surface.

As used herein, the term "substantially free" means less than 0.1 percent by weight, such as less than 0.01 percent by weight, such as less that 0.001 percent by weight, such as 0 percent by weight.

"Therapeutically effective amount," as used herein, is an amount of a pharmaceutically active agent that produces the desired therapeutic response upon oral administration. One skilled in the art can readily determine the therapeutically effective amount (e.g., effective blood levels) of a pharmaceutically active agent for a given patient by considering factors such as, for example, the particular pharmaceutically active agent being administered; the bioavailability characteristics of the pharmaceutically active agent; the dose regimen desired; the age and weight of the patient; and the like.

Pharmaceutically Active Agents

In one embodiment, the tablets of the present invention contains the pharmaceutically active agents cetirizine, pseudoephedrine, and naproxen. The term "cetirizine" includes isomers thereof (such as levocetirizine) and pharmaceutically acceptable salts (such as cetirizine dihydrochloride and levocetirizine dihydrochloride). The term "pseudoephedrine" includes pharmaceutically acceptable salts thereof (such as pseudoephedrine HCl). The term "naproxen" includes pharmaceutically acceptable salts thereof (such as naproxen sodium).

In one embodiment, the tablet contains another decongestant (such as phenylephrine) rather then pseudoephedrine.

The term "phenylephrine" includes pharmaceutically acceptable salts thereof (such as phenylephrine HCl).

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

In one embodiment, the pharmaceutically active agent or agents are present in the tablet in a therapeutically effective amount. In one embodiment, the tablet (e.g., the first drug layer) contains from about 200 to about 250 mg of naproxen sodium; the tablet (e.g., the second drug layer) contains from about 100 to about 150 mg of pseudoephedrine HCl; and the tablet (e.g., the third drug layer) contains from about 4 to about 6 mg of cetirizine dihydrochloride (i.e., cetirizine HCl).

Fluid Bed Granulation of First Powder Mixtures and Third Powder Mixture

In one embodiment, the first powder mixture containing naproxen (used to manufacture the first drug layer of the tablet) is prepared by granulation. In one embodiment, the third powder mixture containing cetirizine (used to manufacture the third drug layer of the tablet) is prepared by granulation. Suitable granulation techniques include, but are not limited to, high shear, fluid bed granulation, roller compaction, and chilsonation.

In one embodiment, the first powder mixture is prepared as a direct compression blend and does not undergo a granulation processing step. In one embodiment, the third powder mixture is prepared as a direct compression blend and does not undergo a granulation processing step.

In one embodiment, the amount of naproxen present in the first powder mixture is from about 30 percent to about 90 percent by weight of the first powder mixture, such as from about 40 percent to about 70 percent.

In one embodiment, the amount of cetirizine present in the third powder mixture is from about 5 percent to about 30 percent by weight of the third powder mixture, such as from about 6 percent to about 20 percent.

The first powder mixture and the second powered mixture may further include other tableting excipients such as fillers, glidants, tablet binders, lubricants, disintegrants and mixtures thereof.

Suitable fillers include, but are not limited to, water-soluble compressible carbohydrates such as sugars (e.g., dextrose, sucrose, maltose, and lactose), starches (e.g., corn starch), sugar-alcohols (e.g., mannitol, sorbitol, maltitol, erythritol, and xylitol), starch hydrolysates (e.g., dextrins, and maltodextrins), and water insoluble plastically deforming materials (e.g., microcrystalline cellulose or other cellulosic derivatives), and mixtures thereof.

Suitable glidants include, but are not limited to, colloidal silicon dioxide.

Suitable tablet binders include, but are not limited to, hydroxypropyl cellulose, microcrystalline wax, carnuba wax, and mixtures thereof.

Suitable lubricants include, but are not limited to, long chain fatty acids and their salts, such as magnesium stearate and stearic acid, talc, glycerides waxes, and mixtures thereof.

Suitable disintegrants include, but are not limited to, sodium starch glycolate, cross-linked polyvinylpyrrolidone, cross-linked carboxymethylcellulose, starches, microcrystalline cellulose, and mixtures thereof. In one embodiment, the powder mixture contains up to about 5 percent by weight of such disintegrant.

Modified Release Second Powder Mixture Containing a Decongestant

In one embodiment, the decongestant is delivered in a modified release manner through a modified release matrix containing a second powder mixture containing (i) pseudoephedrine and/or another decongestant such as phenylephrine and (ii) a water insoluble modified release excipient. Examples of suitable water-insoluble modified release excipients include, but are not limited to, water-insoluble polymers, water-swellable polymers and low-melting hydrophobic materials, and mixtures thereof. In one embodiment, the modified release matrix is prepared as a dry blend. In another embodiment, the modified release matrix is prepared as a granulation. In another embodiment the modified release matrix is prepared as a wet granulation which is dried prior to compression. In one embodiment, the decongestant is released in a zero-order manner. In one embodiment, the decongestant is released in a first-order manner.

Examples of suitable water-insoluble polymers include, but are not limited to, water-swellable celluloses (such as hypromellose), polyalkylene glycols, thermoplastic polyalkylene oxides, acrylic polymers and co-polymers, hydrocolloids, swelling cross-linked polymers, and mixtures thereof. Examples of suitable water swellable celluloses include, but are not limited to, hypromellose, sodium carboxymethylcellulose, hydroxypropylcellulose, cross-linked hydroxypropylcellulose, hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols for use in the modified release matrix include, but are not limited to, polyethylene glycol. Examples of suitable thermoplastic polyalkylene oxides include, but are not limited to, poly (ethylene oxide). Examples of suitable acrylic polymers include, but are not limited to, potassium methacrylatedivinylbenzene copolymer, polymethylmethacrylate, methacrylic ester copolymers, ammonio methacrylate copolymers (such as those commercially available from Evonik Industries under the under the tradename EUDRAGIT® EL and RS), high-molecular weight cross-linked acrylic acid homopolymers and copolymers (such as those commercially available from Noveon Chemicals under the tradename CARBOPOL™ (e.g., having a viscosity of greater than 50,000 centipoise when tested using a Brookfield RVT Viscometer at 25° C., using spindle # 7, when dispersed in a basic solution)). Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof.

Examples off suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their salts, and mixtures thereof. Examples of suitable fatty acid esters include, but are not limited to, sucrose fatty acid esters, mono-, di-, and tri-glycerides, glyceryl behenate, glyceryl palmitostearate, glyceryl monostearate, glyceryl tristearate, glyceryl trilaurylate, glyceryl myristate, lauroyl macrogol-32 glycerides, stearoyl macrogol-32 glycerides, and mixtures thereof. Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, paraffin wax, and mixtures thereof.

In one embodiment, the water insoluble release modifying excipient is the polymer hydroxypropylmethylcellulose, also known as hypromellose (such as those commercially available from the Dow Corporation as Methocel® K3, K4M, K15M, K100M), or hydroxypropyl cellulose (such as those commercially available from Ashland Chemical corporation as Klucel® HXF, HF HPC or Natrosol® HHX or HX HEC), or mixtures thereof.

In one embodiment, the amount of modified release polymer in the second powder mixture is from about 20 percent to about 70 percent, such as from about 35 percent to about 60 percent, by weight of the second powder mixture.

In one embodiment, the second drug layer contains modified release particles of pseudoephedrine and/or another decongestant such as phenylephrine. In one embodiment, the modified release particles are prepared using a modified release coating. In one embodiment, the modified release coating includes at least one modified release polymer such as cellulose acetate, ethylcellulose, or methacrylic polymers, such as those commercially available from Rohm America such as Eudragit® NE-30D, RS, and RL polymers. In one embodiment, the modified release coating further includes a plasticizer. Suitable plasticizers include but are not limited to triethylcitrate, tributyl citrate, propylene glycol, castor oil, and triacetin.

In one embodiment, the amount of pseudoephedrine or other decongestant present in the second powder mixture is from about 10 percent to about 50 percent by weight of the second powder mixture, such as from about 20 percent to about 40 percent.

Modified Release Coated Particle Containing a Decongestant

In one embodiment, the decongestant is delivered in a modified release manner through a coated particle. In one embodiment, the coating is applied to a particle such that the decongestant is delivered over at least 8 hours, such at least 12 hours. Suitable coatings for such use include pH independent polymers such as ethylcellulose, cellulose acetate, and polymethacrylic acid copolymers, such as those commercially available from Rohm America as "Eudragit® RS" and "Eudragit® RL"; copolymers of methacrylic acid esters, such as ethylacrylate methylmethacrylate copolymers available from Rohm Pharma under the tradename "Eudragit® NE 30D".

In one embodiment, the preparation of the core decongestant particle prior to the application of the modified release coating is as those described above and include drug layering and granulation. The modified release coating may also be applied using those techniques described above, including fluidized bed coating and microencapsulation. In one embodiment, the coating is applied at a level from about 10 percent to about 70 percent, such as from about 10 percent to about 40 percent by weight of the coated particle including the decongestant. Other materials may also be included in the coating, such as water soluble polymers, plasticizers, glidants such as colloidal silicon dioxide and talc, and surfactants.

Barrier Layer

In one embodiment, the barrier layer is substantially free of naproxen, pseudoephedrine or another decongestant, and/or cetirizine. In one embodiment, the barrier layer is substantially free of a pharmaceutically active agent. In one embodiment the barrier layer is substantially free of a basic compound. Basic compounds include but are not limited to sodium hydroxide, potassium hydroxide, and magnesium stearate.

In one embodiment, the barrier layer substantially covers both the first drug layer and the second drug layer, and the third drug layer substantially covers the barrier layer. In one embodiment, the second drug layer contains a pseudoephedrine modified release matrix or modified release coated particles containing a decongestant and the first drug layer contains an immediate release naproxen In one embodiment, the barrier layer is applied as a film. When the barrier layer is applied as a film, it may be applied by a spraying, enrobing, or dipping process. In one embodiment, the barrier layer is added by a compression process. In one embodiment wherein the barrier is applied as a sprayed film, the barrier is an immediate release layer. In one embodiment, the sprayed barrier layer includes a sugar. Suitable sugars include but are not limited to sucrose, mannose, fructose, glucose and lactose.

In one embodiment, the barrier layer contains a water soluble polymer. Examples of suitable water-soluble film forming polymers include, but are not limited to, hypromellose, starch, corn starch, modified starch, hydroxypropyl cellulose, methylcellulose, polymethacrylates, polyvinyl alcohol and polyvinyl alcohol blends and polyethylene glycol copolymers. In one embodiment the barrier layer includes gelatin.

In one embodiment a plasticizer is added to the barrier layer film. Suitable plasticizers include but are not limited to polyethylene glycol, propylene glycol, triethylcitrate, tributyl citrate, castor oil, and triacetin. The plasticizer may be added at a level from about 1 percent to about 40 percent, such as from about 5 percent to about 20 percent by weight, of the barrier layer.

In one embodiment the barrier layer is applied as an immediate release compressed powder. In the embodiment wherein the barrier layer is applied as a compressed powder, the barrier layer may contain fillers, glidants, tablet binders, lubricants, or disintegrants.

In one embodiment, the amount of the barrier layer is from about 0.5 percent to about 8 percent, such as from about 1 percent to about 5 percent, by weight of the tablet including the barrier layer. In one embodiment, the thickness of the barrier layer is from about 30 microns to about 200 microns.

Manufacture of Bi-Layer Core Tablet

In one embodiment, the components of the powder are blended together, for example as dry powders, and fed into the die cavity of an apparatus that applies pressure to form a tablet core. Any suitable compacting apparatus may be used, including, but not limited to, conventional unitary or rotary tablet press. In one embodiment, the tablet core may be formed by compaction using a rotary tablet press (e.g., such as those commercially available from Fette America Inc., Rockaway, N.J. or Manesty Machines LTD, Liverpool, UK).

In general, a metered volume of powder is filled into a die cavity (where the powder is either gravity fed or mechanically fed from a feeder) of the rotary tablet press, and the cavity rotates as part of a "die table" from the filling position to a compaction position. At the compaction position, the powder is compacted between an upper and a lower punch, then the resulting tablet core is pushed from the die cavity by the lower punch and then guided to an injection chute by a stationary "take-off" bar.

In another embodiment, the tablet may be prepared by the compression methods and apparatus described in U.S. Patent Application Publication No. 20040156902. Specifically, the tablet core may be made using a rotary compression module including a fill zone, insertion zone, compression zone, ejection zone, and purge zone in a single apparatus having a double row die construction. The dies of the compression module may then be filled using the assistance of a vacuum, with filters located in or near each die. The purge zone of the compression module includes an optional powder recovery system to recover excess powder from the filters and return the powder to the dies.

In one embodiment, the tablet core is prepared by the compression methods and apparatus described in issued U.S. Pat. No. 6,767,200. Specifically, the tablet core is made using a rotary compression module including a fill zone, compression zone, and ejection zone in a single apparatus having a double row die construction as shown in FIG. 6 therein. The dies of the compression module are preferably filled using the assistance of a vacuum, with filters located in or near each die.

The tablet core may have one of a variety of different shapes. For example, the tablet core may be shaped as a polyhedron, such as a cube, pyramid, prism, or the like; or may have the geometry of a space figure with some non-flat faces, such as a cone, truncated cone, cylinder, sphere, torus, or the like. In certain embodiments, a tablet core has one or more major faces. For example, the tablet core surface typically has opposing upper and lower faces formed by contact with the upper and lower punch faces in the compression machine. In such embodiments the tablet core surface typically further includes a "belly-band" located between the upper and lower faces, and formed by contact with the die walls in the compression machine.

In one embodiment, the first powder mixture is compressed at forces from about 0.5 kiloNewtons to about 10 kiloNewtons, such as from about 0.5 kiloNewtons to about 2 kiloNewtons, to form the first drug layer and the second powder mixture is compressed with the first drug layer at forces from about 1 kiloNewtons to about 15 kiloNewtons, such as from about 1 kiloNewtons to about 10 kiloNewtons, to form a two layer tablet core.

In one embodiment, the amount of naproxen present in the first drug layer is from about 30 percent to about 90 percent by weight of the first drug layer, such as from about 40 percent to about 70 percent.

In one embodiment, the amount of pseudoephedrine or other decongestant present in the second drug layer is from about 10 percent to about 50 percent by weight of the second drug layer, such as from about 20 percent to about 40 percent.

In one embodiment, each powder mixture has an average particle size if about 50 microns to about 500 microns, such as between 50 microns and 300 microns.

Third Drug Layer Containing Cetirizine

In one embodiment, the cetirizine is applied as a third drug layer which substantially covers the barrier layer. In one embodiment, the third drug layer is applied as a film. In one embodiment, the third drug layer including cetirizine is applied as a compressed powder. In one embodiment, when the third drug layer is applied as a film, it may be applied by a spraying, enrobing, or dipping process.

In the embodiment where the cetirizine is applied as a film, the cetirizine, a coating agent, and a solvent are combined as a mixture, and the mixture is applied to the barrier layer of the tablet, and the solvent is then dried from the tablet surface. Suitable solvents include but are not limited to water, organic solvents such as ethanol, methanol, isopropanol, acetone, and mixtures thereof. In one embodiment the coating agent is a sugar. Suitable sugars include but are not limited to sucrose, mannose, fructose, glucose and lactose. In one embodiment, the coating agent is gelatin.

In one embodiment, the third drug layer includes cetirizine and a water soluble film-forming polymer as the coating agent. Examples of suitable water-soluble film forming polymers include, but are not limited to, hypromellose, starch, corn starch, modified starch, hydroxypropyl cellulose, methylcellulose, polymethacrylates, polyvinyl alcohol and polyvinyl alcohol blends and polyethylene glycol copolymers. In one embodiment, the third drug layer includes gelatin.

In one embodiment, the amount of the third drug layer is from about 0.5 percent to about 8 percent, such as from about 1 percent to about 5 percent, by weight of the tablet including the third drug layer.

In one embodiment, a plasticizer is added to the third drug layer. Suitable plasticizers include but are not limited to polyethylene glycol, propylene glycol, triethylcitrate, tributyl citrate and triacetin. The plasticizer may be added at a level from about 1 percent to about 30 percent, such as from about 5 percent to about 20 percent, by weight of the third drug layer.

In one embodiment, the amount of cetirizine present in the third drug layer is from about 1 percent to about 40 percent by weight of the third drug layer, such as from about 2 percent to about 20 percent.

In one embodiment, the third drug layer is applied as an immediate release compressed powder. In the embodiment wherein the third drug layer is applied as a compressed powder, the layer may include fillers, glidants, tablet binders, lubricants or disintegrants. In one embodiment, the third drug layer is prepared as a wet granulation with the cetirizine and dried prior to compression.

In one embodiment, the thickness of the third drug layer is from about 30 microns to about 200 microns In one embodiment, the third drug layer is substantially free of a basic compound.

In one embodiment, the amount of p-chlorobenzophenone (p-CBP), a degredant of cetirizine, present in the tablet (i.e., if any) is less than 0.2%, such as less than 0.1%, such as less than 0.05%, by weight of the amount of cetirizine in the tablet following storage of the tablet at 40 degrees Celsius and 75 percent relative humidity for at least 3 months.

Film Coating Tablet

In one embodiment, the tablet core (e.g., the first drug layer, the second drug layer, the barrier layer, and/or the third drug layer) is coated with a protective film coating. In one embodiment, the film coating does not contain a pharmaceutically active agent. In one embodiment, the film coating contains a film-forming polymer that is water-soluble. Examples of suitable water-soluble film forming polymers include, but are not limited to, hypromellose, starch, modified starch, hydroxypropyl cellulose, methylcellulose, polyvinyl alcohol and polyvinyl alcohol and polyethylene glycol copolymers. In one embodiment, the amount of the coating layer is from about 0.5 percent to about 8 percent, such as from about 1 percent to about 5 percent by weight of the coated tablet.

Use of Tablet

In one embodiment, the present invention features a method of treating symptoms of upper respiratory allergies including seasonal allergies and rhinitis (such as due to hay fever) and situational allergies (such as dust and pet allergies), nasal congestion (including sinus congestion), and headache (such as sinus headache) by administering a tablet of the present invention to a person in need to such treatment. Examples of symptoms of upper respiratory allergies include, but are not limited to, runny nose, sneezing, itchy/watery eyes, and itching of the nose or throat.

In one embodiment, the tablet is adapted to maintain a therapeutically effective amount of pseudoephedrine for a period of at least four hours upon ingestion, such as at least eight hours upon ingestion, such as at least twelve hours upon ingestion, such as at least twenty-four hours upon ingestion.

EXAMPLES

Specific embodiments of the present invention are illustrated by way of the following examples. This invention is not confined to the specific limitations set forth in these examples.

Example 1

Preparation of Granulation Containing Naproxen Sodium

The naproxen sodium granulation of Table 1 was prepared as follows. The naproxen sodium, first quantity of croscarmellose sodium and microcrystalline cellulose were placed into a Glatt GPCG 15 fluid bed granulator equipped with a top-spray insert (commercially available from Glatt Air Techniques in Ramsey, N.J.). The granulating solution was prepared by adding hydroxypropyl cellulose to 10 kg of purified water and mixed at 100 RPM for approximately 30 minutes. The solution was then allowed to cool to approximately 30° C.

The granulating solution was sprayed on to the naproxen blend at a spray rate of 60-120 g/minute at a product temperature of approximately 15-25° C., and dried to a final moisture of less than 5% when analyzed using a Computrac® MAX2000XL loss on drying moisture analyzer (commercially available from Arizona Instrument LLC in Chandler, Ariz.) set at 100° C. The dried granules were then screened through a Glatt Quick Sieve equipped with a 1.5 mm screen. The second quantity of croscarmellose sodium, lake color blend and stearic acid were also screened through the Glatt Quick Sieve equipped with a 1.5 mm screen.

The ingredients were blended in a 16 quart twin shell 'V' blender for approximately 150-450 revolutions. The magnesium stearate was then manually passed through a 20 mesh screen and added to the naproxen blend in the 'V' blender, and blended for approximately 100-200 revolutions.

TABLE 1

Naproxen Granulation Formulation

| Material | Mg/ tablet | g/Batch 3.5 kg | % Weight in Granulation |
|---|---|---|---|
| Naproxen Sodium USP | 220.00 | 2.33 | 66.67 |
| Microcrystalline Cellulose NF[1] (Avicel ™ pH 101) | 80.00 | 0.848 | 24.24 |
| Croscarmellose Sodium (1st quantity) | 4.00 | 0.042 | 1.21 |
| Hydroxypropyl Cellulose[2] | 16.00 | 0.170 | 4.85 |

TABLE 1-continued

Naproxen Granulation Formulation

| Material | Mg/ tablet | g/Batch 3.5 kg | % Weight in Granulation |
|---|---|---|---|
| Purified Water[3] | N/A | N/A | N/A |
| Croscarmellose Sodium (2nd quantity) | 4.00 | 0.042 | 1.21 |
| Stearic Acid | 3.20 | 0.034 | 0.97 |
| Lime Green Lake Blend (038-107-2) | 2.00 | 0.023 | 0.61 |
| Magnesium Stearate | 0.80 | 0.008 | 0.24 |
| TOTAL: | 330.0 | | 100.00 |

[1]Commercially available from FMC Corporation in Philadelphia, PA as Avicel ™ pH 101
[2]Commercially available from Ashland Inc in Wilmington, DE as Klucel EF ™
[3]Purified water removed from formulation upon drying Example 2

Preparation of Granulation Containing Cetirizine Dihydrochloride

The cetirizine dihydrochloride granulation of Table 2 was prepared as follows. The microcrystalline cellulose and corn starch from Table 2 were placed into a Glatt GPCG 15 fluid bed granulator equipped with a top-spray insert.

The granulating solution was prepared by adding 10 kg of purified water to a suitable stainless steel vessel and warming the water to 45° C. The hydroxypropyl cellulose was added to the purified water and mixed at 100 RPM for approximately 30 minutes. The solution was then allowed to cool to approximately 30° C. The cetirizine dihydrochloride was then added to the solution and mixed for approximately 30 minutes.

The dried granules were screened through a Glatt Quick Sieve equipped with a 1.5 mm screen. The croscarmellose sodium and stearic acid were also screened through the Glatt Quick Sieve equipped with a 1.5 mm screen.

The ingredients were blended in a 16 quart twin shell 'V' blender for approximately 150-450 revolutions. The magnesium stearate was manually passed through a 20 mesh screen and added to the naproxen blend in the 'V' blender, and blended for approximately 100-200 revolutions.

TABLE 2

Cetirizine Dihydrochloride Granulation Formulation

| Material | Mg/ tablet | g/Batch 3000 | % Weight in Granulation |
|---|---|---|---|
| Cetirizine Dihydrochloride | 5.00 | 176.5 | 5.88 |
| Microcrystalline Cellulose NF[1] | 50.00 | 1764.7 | 58.82 |
| Corn Starch | 21.00 | 741.2 | 24.70 |
| Hydroxypropyl Cellulose[2] | 4.00 | 141.2 | 4.71 |
| Purified Water[3] | N/A | N/A | N/A |
| Croscarmellose Sodium | 4.00 | 141.2 | 4.71 |
| Stearic Acid | 0.80 | 28.3 | 0.94 |
| Magnesium Stearate | 0.20 | 7.1 | 0.24 |
| TOTAL: | 85.0 | 3000 | 100.00 |

[1]Commercially available from FMC Corporation in Philadelphia, PA as Avicel ™ pH 101
[2]Commercially available from Ashland Inc in Wilmington, DE as Klucel EF ™
[3]Purified water removed from formulation upon drying Example 3

Preparation of Sustained Release Pseudoephedrine HCl Layer: Dry Blend and Granulation Part A: Dry Blend Process: The sustained release pseudoephedrine layer of Table 3 was manufactured by a dry blend process as follows. The pseudoephedrine HCl, microcrystalline cellulose, croscarmellose sodium, and colloidal silicon dioxide were passed through a Glatt quick sieve equipped with a 1.5 mm screen. The materials were placed into a 1 cubic foot twin shell 'V' Blender and blended for 150-450 revolutions. The magnesium stearate was manually passed through a 20 mesh screen and added to the naproxen blend in the 'V' Blender, and blended for approximately 100-200 revolutions

TABLE 3

Pseudoephedrine HCl Blend Formulation

| Material | Mg/ tablet | g/Batch 7000 g | % Weight in Blend |
|---|---|---|---|
| Pseudoephedrine HCl | 120.00 | 2800 | 40.00 |
| Microcrystalline Cellulose NF[1] | 57.00 | 1330 | 19.00 |
| Hypromellose USP[2] | 120.00 | 2800 | 40.00 |
| Colloidal Silicon Dioxide | 1.50 | 35 | 0.50 |
| Magnesium Stearate | 1.50 | 35 | 0.50 |
| TOTAL: | 300.00 | 7000 | 100.00 |

[1]Commercially available from FMC Corporation in Philadelphia, PA as Avicel ™ pH 101
[2]Commercially available from Dow Chemical Corporation in Midland Michigan as Methocel K15M CR ™
[3]Purified water removed from formulation upon drying Part B: Pseudoephedrine Granulation Process The sustained release pseudoephedrine layer of Table 3 was also manufactured by a granulation process as follows. The pseudoephedrine, hypromellose, and microcrystalline cellulose from Table 3 were placed into a Glatt GPCG 15 fluid bed granulator equipped with a top-spray insert. 2500 g of purified water was sprayed onto the to the pseudoephedrine, hypromellose, and microcrystalline cellulose blend at a spray rate of 60-80 g/minute at a product temperature of approximately 19-25° C., and dried to a final moisture of less than 4.0% when analyzed using a Computrac® MAX2000 XL loss on drying moisture analyzer set at 100° C. The dried granules were screened through a Glatt Quick Sieve equipped with a 1.5 mm screen. Approximately half of the magnesium stearate and all of the colloidal silicon dioxide were also screened through the Glatt quick sieve equipped with a 1.5 mm screen.

The ingredients were blended in a 16 Quart twin shell 'V' Blender for approximately 150-450 revolutions. The remaining magnesium stearate was manually passed through a 20 mesh screen and added to the pseudoephedrine blend in the 'V' Blender, and blended for approximately 100-200 revolutions.

Example 4

Preparation of Bi-Layer Tablets Including Naproxen and Pseudoephedrine

Approximately 330 mg of the naproxen granulation (bottom layer) from Example 1 and 300 mg of pseudoephedrine (top layer) from Example 3, Part B were compressed into a bilayer tablet using 0.350×0.710 inches, oval, Standard concave tooling at a compression forces of approx. 20 KN using a KORSCH XL400 rotary tablet press.

Example 5

Comparative Example of using a Bi-Layer Tablet with Naproxen and Cetirizine Adjacent Layers In order to evaluate the impact of compressing a tablet with naproxen and cetirizine layers, which are adjacent to one another, tablets were prepared and evaluated on stability.

The naproxen granulation from Example 1 and the cetirizine granulation from Example 2 were compressed into a bi-layer tablet using a rotary tablet press Fette 102i. The order of addition was as such, the first (bottom) layer contained 330 mg of naproxen granulation and 85 mg of the cetirizine granulation, such that the naproxen layer and the cetirizine layers were adjacent to each other. The tablet was compressed using 0.350×0.710 inches, oval, standard concave tooling and a compression force of approximately to 15-20 kiloNewtons.

Example 6

Comparative Example of using a Single Layer Tablet with Blended Naproxen and Cetirizine Granulations In order to evaluate the impact of compressing a tablet with naproxen and cetirizine in a single layered tablet, tablets were prepared as follows. 2385 grams of the naproxen granulation from Example 1 and the 68 grams cetirizine granulation from Example 2 were blended in a "V-Blender" for approximately 10 minutes, discharged and compressed into a single layered tablet using a rotary tablet press Fette 102i. The tablet was compressed using 0.350×0.710 inches, oval, standard concave tooling and a compression force of approximately to 15-20 kiloNewtons.

Example 7

Coating of Bi-Layer Tablet with Barrier Layer Film Coating and Third Drug Layer Containing Cetirizine Part A: Preparation of Barrier Layer Hypromellose Coating Solution: A hypromellose based polymer solution (commercially available from the Colorcon Corporation in West Point, Pa. as Opadry® Clear YS-5-7042) was prepared by adding 400 g of hypromellose to 3600 g of purified water in a suitable stainless steel vessel while mixing at 100 RPM. The polymer was allowed to hydrate and the foam to dissipate (approximately 30 minutes).

Part B: Preparation of Hydroypropyl Cellulose and Cetirizine Coating Solution: Approximately 2585 g of purified water was added to a suitably sized stainless steel container and allowed to warm to 40° C. Approximately 80 g of hydroxypropylcellulose was added while mixing at 100 RPM and mixed for approximately 30 minutes. The solution was allowed to cool to 30° C. 49.2 g of Cetirizine dihydrochloride was added to the solution while mixing.

Part C: Coating of Tablets with Barrier Layer, Cetirizine Coating layer, and outer Coating Layer Approximately 4500 g of coated BiLayer tablets from Example 4 were added top an Accela® Coater tablet coater (commercially available from Thomas Engineering, inc. in Hoffman Estates, Ill.). For the first coating layer, approximately 1350 g of hypromellose solution prepared according to Example 7, Part A were added to the tablets at a spray rate of approx 15 g/minute and a product temperature of 30-45° C. The tablets were coated to a weight gain of approximately 2-4 percent. For the cetirizine coating layer, the hydroxypropyl cellulose and cetirizine solution from Example 7, Part B was then sprayed onto the tablets for a weight gain of approximately 3 percent. The hydroxypropylcellulose and cetirizine solution was sprayed at a spray rate of 10-20 g/minute and a product temperature of 30-45° C.

An additional for coating layer not containing cetirizine was added on top of the cetirizine layer to a weight gain of approximately 3 percent, using 1350 g of hypromellose solution (prepared according to Example 7, Part A). This solution was sprayed at approximately 10-20 g/minute and a product temperature of 30-45° C.

Part D: Application of Hypromellose Coating Solution to Bi-Layer Tablets (Comparative Example) Approximately 200 g of the bi-layer Tablets from Example 5 were added to a Accela® Coater tablet coater. They were coated using 55 g of solution from Example 7, Part A at a spray rate of approximately 15 g/minute and a product temperature of 45° C. to a 2-4 percent weight gain.

Part E: Application of Hypromellose Coating Solution to Single Layer tablets (Comparative Example) Approximately 200 g of the single layer Tablets from Example 6 were added to an Accela® Coater tablet coater (commercially available from Thomas Engineering, Inc. in Hoffman Estates, Ill.). They were coated using 55 g of solution from Example 7, Part A at a spray rate of approximately 15 g/minute and a product temperature of 45° C. to a 2-4 percent weight gain.

Example 8

Dissolution Data

Part A: Deionized Water Dissolution Media Analysis: The coated tablets produced in Example 7, Part C were placed into United States Pharmacopeia (USP) Type II apparatus (Paddles, 50 RPM) containing 900 mL of deionized water at 37° C. 10 mL samples were removed from each vessel at 30 minutes, 45 minutes, 1, 2, 3, 4, 8, 10 and 12 hours and analyzed for pseudoephedrine by UV spectroscopy. The average of 6 tablets is reported in Table 4.

TABLE 4

Dissolution Data of Tablets

| Time point | Tablets % Released |
|---|---|
| 30 minutes | 28 |
| 45 minutes | 39 |
| 1 hour | 44 |
| 2 hours | 70 |
| 3 hours | 86 |
| 4 hours | 94 |
| 6 hours | 100 |
| 8 hours | 102 |
| 10 hours | 102 |
| 12 hours | 101 |

The data demonstrates that the tablets had an extended release dose from 30 minutes through 12 hours.

Example 9

Stability Analysis and Data

The tablets from Example 7, Part C and the bi-layer tablets prepared as a comparative example in Example 7, Part D (wherein the cetirizine and naproxen layers were adjacent to one another), and the single layer tablets prepared as a comparative example in Example 7, Part E (wherein the cetirizine and naproxen granulations are blended in one layer) were packaged in plastic blister packaging and evaluated for degradation levels at various stability time points. P-chlorobenzophenone (p-CBP) was identified as the most prevalent degradant of interest when cetirizine and basic compounds (such as naproxen) are in contact with each other. Basic compounds have the potential to remove the HCl portions of the cetirizine dihydrochloride molecule and cause the formation of p-CBP. The level of para-chlorobenzophenone was analyzed at 1 month, 2 months and 3 months in 2 conditions: 25° C. and 60% relative humidity (RH) and 40° C. and 75% relative humidity and shown in Table 5. As indicated in Table 5, applicants discovered that the level of degradation was significantly higher in the samples where the compressed naproxen and cetirizine layers are adjacent to each other (i.e., the comparative example).

A high-pressure liquid chromatography (HPLC) method was used to analyze the level of degradation. In order to perform the analysis, an 150×4.6 mm C8 HPLC column was used and the temperature was kept at 33° C. A gradient analysis was performed with a mobile phase containing 20 mM phosphate buffer (pH 6.0) and acetonitrile, using a mixture ratio from 80:20 to 45:55. A pump flow rate of 1.0-1.3 mL/minute and an injection volume of 40 μL was used. The UV detector was set at a wavelength of 230 nanometers from 0 to 21 minutes, and 260 nanometers from 21 to 35 minutes.

TABLE 5

Stability Data

| Sample | Stability Time point | Storage Condition | % Para-chlorobenzo-phenone |
|---|---|---|---|
| Tablet[1] | 1 month | 25° C./60% RH | ND |
|  |  | 40° C./75% RH | 0.04 |
|  | 2 months | 25° C./60% RH | 0.03 |
|  |  | 40° C./75% RH | 0.06 |
|  | 3 months | 25° C./60% RH | 0.04 |
|  |  | 40° C./75% RH | 0.08 |
| Comparative Bi-Layer Tablet[2] | 1 month | 25° C./60% RH | 0.03 |
|  |  | 40° C./75% RH | 0.06 |
|  | 2 months | 25° C./60% RH | 0.04 |
|  |  | 40° C./75% RH | 0.10 |
|  | 3 months | 25° C./60% RH | 0.04 |
|  |  | 40° C./75% RH | 0.15 |
| Comparative Single Layer Tablet[3] | 1 month | 25° C./60% RH | 0.06 |
|  |  | 40° C./75% RH | 0.30 |
|  | 2 months | 25° C./60% RH | 0.10 |
|  |  | 40° C./75% RH | 0.49 |
|  | 3 months | 25° C./60% RH | 0.12 |
|  |  | 40° C./75% RH | 0.64 |

[1]Includes naproxen layer, sustained release pseudoephedrine layer in bilayer core, and outer sprayed film coating including cetirizine
[2]Includes adjacent naproxen and cetirizine layers
[3]Includes naproxen and cetirizine in the same layer
ND—None Detected It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A tablet comprising:
   (i) a first drug layer comprising naproxen;
   (ii) a second drug layer comprising pseudoephedrine wherein said second drug layer is a sustained release layer adapted to deliver a therapeutically effective amount of pseudoephedrine for a period of at least twelve hours;
   (iii) a barrier layer that does not comprise naproxen, wherein said barrier layer is in contact with said first drug layer; and
   (iv) a third drug layer comprising cetirizine, wherein said third drug layer is in contact with said barrier layer and is not in contact with said first drug layer.

2. A tablet of claim 1, wherein said first drug layer is in contact with said second drug layer, wherein said barrier layer substantially covers both said first drug layer and said second drug layer, and wherein said third drug layer substantially covers said barrier layer.

3. A tablet of claim 1, wherein said first drug layer comprises from about 200 to about 250 mg of naproxen sodium, said second drug layer comprises from about 100 to about 150 mg of pseudoephedrine HCl, and said third drug layer comprises from about 4 to about 6 mg of cetirizine dihydrochloride.

4. A tablet of claim 2, wherein said first drug layer comprises from about 200 to about 250 mg of naproxen sodium, said second drug layer comprises from about 100 to about 150 mg of pseudoephedrine HCl, and said third drug layer comprises from about 4 to about 6 mg of cetirizine dihydrochloride.

5. A tablet of claim 1, wherein said second drug layer comprises hypromellose.

6. A tablet of claim 2, wherein said second drug layer comprises hypromellose.

7. A tablet of claim 3, wherein said second drug layer comprises hypromellose.

8. A tablet of claim 4, wherein said second drug layer comprises hypromellose.

9. A tablet of claim 1, wherein said tablet further comprises an outer coating comprising a water-soluble film-forming polymer.

10. A tablet of claim 1, wherein the amount of p-chlorobenzophenone present in the tablet is less than 0.2%, by weight, of the amount of cetirizine in the tablet following storage of the tablet at 40 degrees Celsius and 75 percent relative humidity for at least 3 months.

11. A method of manufacturing a tablet of claim 1, wherein said method comprises:
    (i) preparing a first powder mixture comprising naproxen utilizing a granulation process;
    (ii) preparing a second powder mixture comprising pseudoephedrine utilizing a granulation or a dry blending process;
    (iii) compressing said first powder mixture together with said second powder mixture to form a tablet core such that said first powder mixture forms said first drug layer and said second powder mixture forms said second drug layer;
    (iv) applying a barrier layer to said tablet core; and
    (v) applying a third drug layer comprising cetirizine to said barrier layer.

12. A method of claim 11, wherein said method of applying said third drug layer comprises applying a solution comprising said cetirizine to said barrier layer.

13. A method of claim 11, wherein said method of applying said third drug layer comprises compressing a powder comprising said cetirizine to said barrier layer.

14. A method of claim 11, wherein said barrier layer substantially covers both said first drug layer and said second drug layer, and said third drug layer substantially covers said barrier layer.

15. A method of claim 14, wherein said first drug layer comprises from about 200 to about 250 mg of naproxen sodium, said second drug layer comprises from about 100 to about 150 mg of pseudoephedrine HCl, and said third drug layer comprises from about 4 to about 6 mg of cetirizine dihydrochloride.

16. A method of claim 11, wherein said second drug layer comprises hypromellose.

17. A method of claim 11, wherein said method further comprises spray coating said third drug layer with a coating solution comprising a water-soluble film-forming polymer.

18. A method of treating symptoms of upper respiratory allergies, nasal congestion, and headache for at least twelve hours, said method comprising administering a tablet of claim 1 to a person in need to such treatment.

19. A method of claim 18, wherein said barrier layer substantially covers both said first drug layer and said second drug layer, and said third drug layer substantially covers said barrier layer.

20. A method of claim 19, wherein said first drug layer comprises from about 200 to about 250 mg of naproxen sodium, said second drug layer comprises from about 100 to about 150 mg of pseudoephedrine HCl, and said third drug layer comprises from about 4 to about 6 mg of cetirizine dihydrochloride.

* * * * *